United States Patent [19]

Rule et al.

[11] Patent Number: 4,778,940
[45] Date of Patent: Oct. 18, 1988

[54] PROCESS FOR PREPARING IODINATED SUBSTITUTED AROMATIC COMPOUNDS

[75] Inventors: Mark Rule; Gerald C. Tustin; Donald W. Lane; Thomas H. Larkins, all of Kingsport, Tenn.

[73] Assignee: Eastman Kodak Company, Rochester, N.Y.

[21] Appl. No.: 29,897

[22] Filed: Mar. 25, 1987

[51] Int. Cl.$^4$ .................................................. C07C 17/15
[52] U.S. Cl. ...................................... 570/203; 570/206; 570/208
[58] Field of Search ........................ 570/206, 208, 203

[56] References Cited

U.S. PATENT DOCUMENTS

| | | | |
|---|---|---|---|
| 3,363,010 | 1/1968 | Schwarzenbek | 570/203 |
| 3,600,331 | 8/1971 | Ingwalson | 570/203 |
| 3,644,542 | 2/1972 | Prahl et al. | 570/203 |
| 4,240,987 | 12/1980 | Martin et al. | 570/206 |
| 4,391,785 | 7/1980 | Rosinski et al. | 502/77 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/206 |
| 77631 | 5/1982 | Japan | 570/206 |
| 159496 | 12/1968 | U.S.S.R. | 570/206 |

OTHER PUBLICATIONS

Groggins, "Unit Processes in Organic Chemistry" Fifth Ed. McGraw-Hill Book Co., Inc. (1958) p. 262.

*Primary Examiner*—Werren B. Lone
*Attorney, Agent, or Firm*—Charles R. Martin; William P. Heath, Jr.

[57] ABSTRACT

A process for iodinating an aromatic compound in which a source of iodine is reacted with the aromatic compound in the presence of oxygen over a non-acid catalyst wherein the aromatic compound has a fluoro, chloro, bromo, iodo, hydroxy or cyano group.

4 Claims, No Drawings

PROCESS FOR PREPARING IODINATED SUBSTITUTED AROMATIC COMPOUNDS

BACKGROUND OF THE INVENTION

1. Field of the Invention

The present invention relates to processes for iodinating substituted aromatic compounds over non-acid catalysts.

2. Discussion of Background

It has long been desired to be able to derivatize aromatic compounds and in particular condensed ring aromatic compounds in commercially attractive quantities since many of these compounds possess properties which would fill long sought needs. In particular, substituted benzene and naphthalene carboxylic acids or esters are particularly desired for use in the manufacture of polyesters which would have excellent properties when fabricated into films, bottles or coatings. However, known techniques for producing these carboxylic acids and esters are very expensive and impractical for commercial exploitation.

DESCRIPTION OF THE PRIOR ART

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Pat. No. 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese Patent Publication 82/77631 in the absence of any oxidizing agent.

Ishida and Chono in Japanese Kokai No. 59/219241 have suggested a technique for oxyiodinating benzene over very acidic zeolite catalyst having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

OTHER INFORMATION

Subsequent to the present invention, Paparatto and Saetti disclosed in European Patent Application Nos. 181,790 and 183,579 techniques for oxyiodination of benzene over zeolite catalysts. European Patent Application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours. European Patent Application No. 183,579 suggests the utilization of X type of Y type of zeolite in non-acid form. According to 183,579 the X or Y zeolites have to be used in the form exchanged with mono-valent, bivalent or trivalent cations and in particular with alkaline or rare earth cations. The techniques of 181,790 and 183,579 prepare the monoiodobenzene in selectivities in excess of 90% and only distinctly minor amounts of the diiodobenzene compounds.

RELATED APPLICATIONS

Copending applications Ser. Nos. 912,806, filed Sept. 29, 1986; 029,959 filed Mar. 25, 1987; 029,898 filed Mar. 25, 1987 disclose techniques for iodinating aromatic compounds over non-acid catalysts. Copending applications Ser. Nos. 029,899 filed Mar. 25, 1987; 029,956 filed Mar. 25, 1987; and 029,949 filed Mar. 25, 1987 disclose traniodination/isomerization reactions which may be used in conjunction with an oxyiodination reaction.

The disclosures of these applications are incorporated herein by reference.

These applications do not address the iodination of substituted aromatics, however. A need exists for a technique by which substituted aromatics may be iodinated.

BRIEF DESCRIPTION OF THE INVENTION

Accordingly, one object of the present invention comprises the technique for catalytically iodinating substituted aromatic compounds.

Another object comprises a process for the selective iodination of substituted benzenes over a zeolite catalyst.

A further object of the present invention comprises the technique of the iodination of substituted naphthalenes over a zeolite catalyst.

These and further objects of the present invention which will become apparent from the following disclosure have been attained by a process which comprises reacting a substituted aromatic compound over a non-acid catalyst with a source of iodine and a source of molecular oxygen.

DESCRIPTION OF THE PREFERRED EMBODIMENTS

The aromatic compounds which can be utilized in practice of the present invention are essentially any substituted aromatic compounds. Here a substituent is considered to be a terminal group replacing hydrogen on the parent aromatic species. Suitable aromatic compounds include hydrocarbon aromatics, nitrogen containing aromatics and sulfur containing aromatics. Typical hydrocarbon aromatics include benzene and biphenyl; condensed ring aromatics such as naphthalene and anthracene; sulfur containing aromatics including thiophene and benzothiophene; nitrogen containing aromatics including pyridine and benzopyridine; and oxygen containing aromatics including furan and benzofuran. Other parent aromatics include diaryl sulfones, diaryl ethers, diaryl carbonyls, diaryl sulfides and the like. Preferred parent aromatics are benzenes, biphenyls and naphthalenes.

Substituents on aromatic compounds which are suitable for the process of the present invention include fluoro, chloro, bromo, iodo, hydroxy, and cyano. Aromatic compounds substituted by alkyl groups are generally not preferred for utilization in the present technique. It has been found that with alkyl substituted aromatics the products are iodinated not only on the ring but also on the side chains. Thus, while alkyl substituted aromatics can be utilized in the present technique their use is not preferred.

The catalyst which may be employed in the present technique are described in copending applications Ser. Nos. 029897, filed Sept. 29, 1986, 029899, filed 3-25-87. The disclosure of these applications incorporated herein by reference for a more complex description of the catalyst in reaction conditions which are to be employed.

The catalysts utilized in the present technique are generally characterized by containing non-acid sites, and more preferably basic sites. The most preferred catalyst for use in one present invention are zeolites in the non-acid form. The zeolites which are chosen must have a pore size at least equal to about the apparent size of the molecule of the substituted aromatic ring compound being reacted. Benzene as well as naphthalene have apparent ring sizes of about 6 Å and this the lower limit on the pore size of the zeolite catalyst which is useful. If the aromatic compound cannot enter into the pore on the zeolite catalyst then only very little conversion of the aromatic compounds will occur. Further, if the zeolite is in the acid form, excessive combustion or oxidation of the aromatic compound will occur which is not preferred. Hence, the preferred zeolites are all in the non-acid form and all contain a pore size of about 6 Å or larger.

The type of zeolite which is utilized is not critical so long as greater than 10% of the exchangeable cations are alkali, alkaline earth or rare earth metals and the pore size is greater than about 6 Å. In general, the reaction rate is a function of silicon to aluminum ratio in the zeolite, since aluminum is part of the active site. It is preferred to use zeolites of with a silicon (as Si) to aluminum (as Al) ratio of 10:1 or less, more particularly 5:1 or less, still more preferred are those zeolites having a silicon to aluminum ratio of 3:1 or less with the most preferred type having a silicon to aluminum ratio of 1.5 or less. Particular types of zeolites which have proven useful are the X and Y types. The Y type zeolite generally has a silicon to aluminum ratio of about 1.5 to 1 to 3:1. The X type zeolite is generally considered to have a silicon to aluminum ratio of about 1:1 to 1.5:1. The X type zeolite exhibits more sensitivity to the counter ion than the Y type does. That is, the selectivity of this X type zeollite to the production of specific mono, di or tri iodinated aromatic compounds can be altered more successfully with the selection of the appropriate counter ions than can the Y type. While not being bound to any particular theory it is believed that the counter ion affects the selectivity by altering the shape of the active site thereby increasing or decreasing the selectivity of the catalyst for any particular isomer as compared with the standard sodium form. As a number of cations at the active site decreases their influence in the shape of the pore decreases and thus selectivity decreases. Thus, when one desires to produce a particular isomer high alumina content zeolites are preferred.

Most of the commercially available zeolites are in the sodium form. The counter ion is easily changed in the zeolite by simple ion exchange and is well known to those skilled in the art. This is generally accomplished by contacting in an aqueous medium a salt of desired counter ion and the zeolite. The period of time over which the contact is conducted and a number of times the ion exchange process is performed is dependent upon the degree of replacement which is desired.

When the aromatic compound is a condensed ring aromatic such as a substituted naphthalene, it is preferred that the zeolite contains sodium, potassium, rubidium and/or cesium counter ions and more preferably potassium, rubidium or cesium counter ions. It has been found that when the zeolite is ion exchanged with lithium, calcium, strontium, barium or rare earth metals the condensed ring aromatics are oxidized by the oxygen present in the gas stream to a higher degree. With potassium, rubidium and cesium counter ions present the degree of naphthalene oxidation is significantly less than 1% of the substituted naphthalene iodinated. That is, essentially no oxidation of naphthalene occurs with these counter ions. When the zeolite is essentially in the sodium form, oxidation of the naphthalene occurs but to a lesser extent than with lithium, calcium, strontium, barium and rare earth metal counter ions.

Other compounds which have been proven useful as catalysts in the present invention are non-zeolitic and are characterized as containing alkali or alkaline earth salts. Typical catalysts include magnesium oxide on silica, calcium aluminate, magnesium aluminate, potassium chloride on alumina, sodium sulfate on silica and the like. These catalysts may be supported or unsupported or bound together with a binder to form a shaped particle. Typical supports and binders include silica, aluminum, various clays and the like. In general, any material not containing acid sites can be utilized as the catalyst support. These non-zeolite catalysts generally do not exhibit the selectivity of the zeolite catalyst when producing polyiodated products.

The temperature which the reaction is to be conducted is not critical and can be any temperature at which when the aromatic compound is fluid. The maximum temperature at which the process can be carried out is that at which combustion of the aromatic compound occurs. Generally, temperatures of from about 100° to 500° C. have been found satisfactory, with temperatures of from 200° to 400° C. being preferred, more preferably from about 200° to 350° C.

The pressure which the process is conducted is not critical and can range from subatmospheric to superatmospheric. The utilization of elevated pressures in the gas phase process may be preferred so as to minimize equipment size. In general, pressures from atmospheric to 600 psig have proven satisfactory although higher or lower pressures can be utilized. The reaction may be conducted in either the liquid or the vapor phase.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the catalyst to its active form once the iodination reaction has occurred. Thus, the amount of oxygen present during the reaction is not critical. However it is preferred that at least $\frac{1}{2}$ mole of oxygen be used for every mole of iodine. The molar ratio of iodine to aromatic compound which is to be reacted is largely determined by whether one desires to produce a monoiodinated aromatic product or polyiodinated aromatic product. Stoichiometrically, $\frac{1}{2}$ mole of iodine reacts with 1 mole of aromatic compound to produce the monoiodinated form. Similarly, on a stoichiometric basis 1 mole of iodine is required to convert 1 mole of aromatic compound to the diiodinated form. Greater or lesser quantities of iodine can be utilized as the artisan may desire. In general, it is desired to run the process to obtain as close to 100% conversion of the iodine as practical so as to simplify the purification steps in the recovery of any unreacted iodine. Suggested mole ratios of aromatic compound to iodine to oxygen are from 1:0.5:0.25 to about 1:2:3.

Essentially any source of iodine may be employed including elemental iodine ($I_2$), hydroiodic acid in gaseous form, or alkyl iodides, preferably lower alkyl iodides. Furthermore, mixtures of these materials may be used as the source of iodine.

It is anticipated that the present process would be carried out continuously by the continuous addition of iodine, oxygen and aromatic compound to the reactor, however, the process can be carried out on a batch or semi batch process as desired. Further, aromatic compound of iodine can be reacted over the catalyst to produce the iodinated product, the addition of the aromatic compound and iodine then being terminated and oxygen then added to the reactor to regenerate catalyst to its active form and then the process commenced again. Alternatively, in a continuous process it is possible to utilize two reactants, circulating the catalyst betwen them. In the first reactor the iodine and aromatic compound would be added and reacted to form the iodinated compound. The catalyst would then be circulated to the second reactor where it would be contacted with oxygen to be regenerated and then recycled to the first reactor to catalyze additional reactions of aromatic compound with iodine.

The space velocity of the process is not critical and may be readily selected by the artisan. Gas hourly space velocity is between 10 and 50,000, preferably between 100 and 20,000 liters per hour of reagents per liter of active zeolite have proven satisfactory.

The catalyst is proven to have an extremely long life and degrades only slowly with time. The degradation of the catalyst is believed to be caused by the decomposition of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite. However, when the catalyst becomes deactivated reactivation is simple. An excellent regeneration technique comprises passing air or oxygen over the catalyst for several hours at elevated temperatures. Typically the temperature is above 400° C. although higher or lower temperatures are proven equally satisfactory. The temperature need only be high enough so as to ensure combustion of the carbon deposit on the catalyst. When pure oxygen is employed lower temperatures can be utilized, while when air is employed temperatures on the order of about 400° C. have proven satisfactory.

The following examples are presented to illustrate the present invention but are not intended in any way to limit the scope of the invention which is defined by the appended claims.

In the following examples, 50 cc of the stated catalyst was placed in a quartz reactor tube with an internal thermowell. The tube was heated with an electric furnace while the reactants were added dropwise over the catalyst bed at a rate of 1 ml/min. Air was fed cocurrently at 300 ml/min. Products were collected by condensing against cold water and identified by gas chromatography-mass spectrometry and quantified by gas chromotography (reported as mole %). All feeds were 0.0341 moles of iodine per mole of aromatic. A high reaction temperature relative to the furnace temperature indicates considerable combustion of the aromatic species has occurred, as does a high % $CO_2$ in the reaction offgas.

EXAMPLE 1

Catalyst: NaX
Furnace temp: 300 deg C.
Reaction temp: 302 deg C.
Aromatic cpd: benzene The reaction product contained 93.1 benzene, 6.8% iodobenzene, and 0.1% diiodobenzene. The offgas contained <0.2% $CO_2$ and iodine conversion was 100%.

EXAMPLE 2

Catalyst: NaX
Furnace temp: 300 deg C.
Reaction temp: 302 deg C.
Aromatic cpd: chlorobenzene The reaction product contained 93.2% chlorobenzene, 6.6% chloroiodobenzene, and 0.2% diiodochlorobenzenes. The offgas contained <0.2% $CO_2$ and iodine conversion was 100%.

EXAMPLE 3

Catalyst: NaX
Furnace temp: 300 deg C.
Reaction temp: 450 deg C.
Aromatic cpd: toluene The reaction product contained greater than 15 separate species. The reaction product was dark and the catalyst deactivated after two hours. The offgas contained 15% $CO_2$.

EXAMPLE 4

Catalyst: NaX
Furnace temp: 200 deg C.
Reaction temp: 220 deg C.
Aromatic cpd: phenol The reaction product contained 92.7% phenol, 1.5% p-iodophenol and 5.8% o-iodophenol. The iodine conversion was 100% and the offgas contained less than 0.1% $CO_2$.

EXAMPLE 5

Catalyst: NaX
Furnace temp: 300 deg C.
Reaction temp: 308 deg C.
Aromatic cpd: benzonitrile The reaction product contained 98.5% benzonitrile, 0.7% p-iodobenzonitrile, 0.4% m-iodobenzonitrile, and 0.2% o-iodobenzonitrile. Iodine conversion was 21%.

EXAMPLE 6

Catalyst: 10% KCl-Al2O3
Furnace temp: 300 deg C.
Reaction temp: 302 deg C.
Aromatic cpd: 1-chloronaphthalene The reaction product contained 95.1% 1-chloronaphthalene and 4.9% chloroiodonaphthalenes. The iodine conversion was 70%.

COMPARATIVE EXAMPLE 7

Catalyst: NaX
Furnace temp: 300 deg C.
Reaction temp: 302 deg C.

Aromatic cpd: nitrobenzene

The reaction product contained over 99% nitrobenzene, with traces of iodobenzene and benzene. Nitrobenzene appears to be unreactive under these conditions.

EXAMPLE 8

Catalyst: NaX
Furnace temp: 300 deg C.
Reaction temp: 302 deg C.
Aromatic cpd: benzophenone The reaction product contained 95.2% benzophenone and 4.7% iodobenzophenones. The iodine conversion was 67% and the offgas contained less than 0.1% $CO_2$.

EXAMPLE 9

Catalyst: NaX
Furnace temp: 300 deg C.
Reaction temp: 306 deg C.
Aromatic cpd: pyridine The reaction product contained 97.2% pyridine and 2.8% iodopyridines. The iodine conversion was 40%.

While the invention has been described in detail with particular reference to preferred embodiments thereof, it will be understood that variations and modifications can be effected within the spirit and scope of the invention.

We claim:

1. A process for mono- or diiodinating an aromatic compound which comprises reacting iodine with the aromatic compound in the presence of oxygen over a zeolite catalyst containing as counter ions sodium, potassium, rubidium, cesium, or mixtures thereof, and wherein:
   (a) the aromatic compound is selected from the group consisting of benzene, biphenyl, terphenyl, naphthalene, anthracene, thiophene, benzothiophene, diphenyl sulfone, diphenyl sulfide, diphenyl ether, pyridine, benzopyridine and benzophenone; and
   (b) the aromatic compound has at least one substituent selected from the group consisting of fluoro, chloro, bromo, iodo, hydroxyl or cyano.

2. The process of claim 1 wherein said zeolite is the 13X type which has been ion exchanged with at least one of potassium, rubidium or cesium.

3. The process of claim 1 wherein said aromatic compound is a substituted benzene.

4. The process of claim 1 wherein said aromatic compound is a substituted naphthalene.

* * * * *